United States Patent [19]

Kossoff et al.

[11] 4,176,658
[45] Dec. 4, 1979

[54] ULTRASONIC ECHOGRAM DISPLAY

[75] Inventors: George Kossoff, Northbridge; David E. Robinson, Avalon Beach, both of Australia

[73] Assignee: The Commonwealth of Australia, Phillip, Australia

[21] Appl. No.: 575,714

[22] Filed: May 8, 1975

[51] Int. Cl.² .................... A61B 10/00; G01N 29/00
[52] U.S. Cl. ...................... 128/660; 73/597; 73/599; 73/602
[58] Field of Search .......... 128/2 V, 2.05 Z; 340/1 R; 73/67.7, 67.8 R, 67.8 S, 67.9, 597, 599, 602

[56] References Cited

U.S. PATENT DOCUMENTS

| | | | |
|---|---|---|---|
| 3,156,110 | 11/1964 | Clynes | 128/2 V X |
| 3,696,324 | 10/1972 | Baum | 73/67.7 X |
| 3,771,355 | 11/1973 | Sachs | 128/2 V X |
| 3,864,661 | 2/1975 | Ranalli | 340/1 R |
| 3,909,771 | 9/1975 | Pickering et al. | 340/1 R |

OTHER PUBLICATIONS

"Early Cancer Diagnosis Through Ultrasonics", Kikuchi et al., in The Journal of the Acoustical Society of America, vol. 29, No. 7, Jul. 1957, pp. 825-833.

*Primary Examiner*—Anton O. Oechsle

[57] ABSTRACT

A method of displaying information obtained by pulse-echo ultrasonic examination of an object, particularly in medical diagnostic examination, comprises forming a first display representing the positions of acoustic impedance discontinuities within the object and simultaneously incorporating in the display other parameters relating to the object.

2 Claims, 2 Drawing Figures

ULTRASONIC ECHOGRAM DISPLAY

This invention relates to the technique of ultrasonic echoscopy of objects and in particular to improvements in techniques used to display information obtained by ultrasonic pulse-echo examination of such objects. The invention is particularly, but not solely, directed to the display of data acquired in medical diagnostic examination using this technique.

Ultrasonic echoscopy provides information about an examined object which may be displayed in the form of an ultrasonic echogram. Such an echogram consists of a display of acoustic impedance discontinuities or reflecting surfaces in the object. It is obtained by directing a short pulse of ultrasonic energy, typically in the 1–30 MHz frequency range, into the examined object where any acoustic impedance discontinuities in the object reflect and return some of the energy in the form of an echo. This echo is received, converted into an electric signal and displayed as an echogram on a cathode ray oscilloscope, a film, a chart or the like.

The echogram may constitute either a one dimensional or a two dimensional representation and in both cases the information is contained in the position and magnitude of the echo displayed. In a one dimensional display, the position along a base line is used to indicate the distance to the reflecting surface whilst the magnitude of the echo is displayed, for example, as a deflection of the base line or as an intensity change. In a two dimensional display, the position along a base line is used to indicate the distance to the reflecting surface as in a one dimensional display, and the direction of the base line is used to represent the direction of propagation of the acoustic energy. The two dimensional display is obtained by changing this direction of propagation of the acoustic energy and by instituting a similar but not necessarily identical movement of the base line of the display. The magnitude of the echo is displayed as for a one dimensional display; for example, as a deflection of the base line or as an intensity change.

The technique of ultrasonic echoscopy is used in medical diagnosis to obtain information about the anatomy of patients. The application of this technique is now widely investigated and is described, for example, by D. E. Robinson in Proceeding of the Institution of Radio and Electronics Engineers Australia, Vol. 31, No. 11, pages 385–392, November 1970: "The Application of Ultrasound in Medical Diagnosis". As pointed out in this article, ultrasonic echoscopy may be used to produce displays resembling anatomical cross-sections which have proved clinically useful when the desired information concerns physical dimensions, shapes of organs or structures or the like. Ultrasonic echography has proved of particular value as a diagnostic aid in the abdomen and pregnant uterus, eye, breast, brain, lung, kidney, liver and heart, these being areas of soft tissue with little bone and air. In general, the technique is considered to complement other techniques to provide a more complete picture of the patients condition, however particularly in pregnancies, ultrasonic echoscopy may be useful in place of X-rays where the latter may not give sufficient information or may be dangerous. In medical use, a pulse of ultrasonic energy is transmitted into a patient in a known direction and echoes are received from reflecting surfaces within the body. The time delay between a transmitted pulse and the received echo depends on the distance from the transmitter to the reflecting surface and the distance information so obtained may be displayed in a suitable way for interpretation and clinical use as a one dimensional range reading or as a two dimensional cross section as previously described.

Particularly in medical diagnostic examination, the usual display technique is to display as a light area on a dark background, or a dark area on a light background, the parts in the scanned area of the patient which contain reflections of ultrasonic energy. As previously described, the only parameter displayed is echo amplitude, which is influenced by the reflection coefficient of the interface and the geometry of the interface. Thus a black and white picture with more or less grey scale is obtained which resembles a picture of the physical cross-section of the part examined.

Techniques are becoming available for obtaining information other than simply position of reflecting interface and amplitude of reflected signal as used at present. A copending application by the inventors describes methods for obtaining velocity of propogation and scattering (roughness) information (U.S. application Ser. No. 367,628, filed June 6, 1973, now abandoned). A method of measurement of absorption has also been published by R. A. Mountford and P. N. T. Wells, "Ultrasonic Liver Scanning: The Quantitative Analysis of the Normal A-Scan", Phys. Med. Biol., 1972, Vol. 17, No. 1, pages 14–25. Further the relationship of echo amplitude as a function of angle has been reported to differ for different materials by C. R. Hill, "Interactions of ultrasound with tissues", Ultrasonics in Medicine, Proc. 2nd World Congress on Ultrasonics in Medicine, Rotterdam, The Netherlands, June 4–8, 1973, Edited by M. de Vlieger, D. N. White and V. R. McCredy, Excerpta Medica, Amsterdam. All of these require some computational means to determine the parameters concerned, and the preferred method is to use a general purpose minicomputer.

It is a principal object of the present invention to provide a method whereby the information obtained by such techniques can be made available on a visual display in a more useful form, especially for medical diagnosis.

According to the present invention, there is provided a method of displaying information obtained by ultrasonic echoscopic examination of an object which comprises forming a first display of information representative of the position of acoustic impedance discontinuities within said object, and simultaneously displaying in said first display information representative of additional parameters of said object.

A considerable increase in diagnostic information can be made available in accordance with the present invention by the use of various types of information display to allow the distribution in the cross-section of two or more parameters to be displayed simultaneously. The display types referred to include grey scale, cross-hatching and colour.

Figure 1:
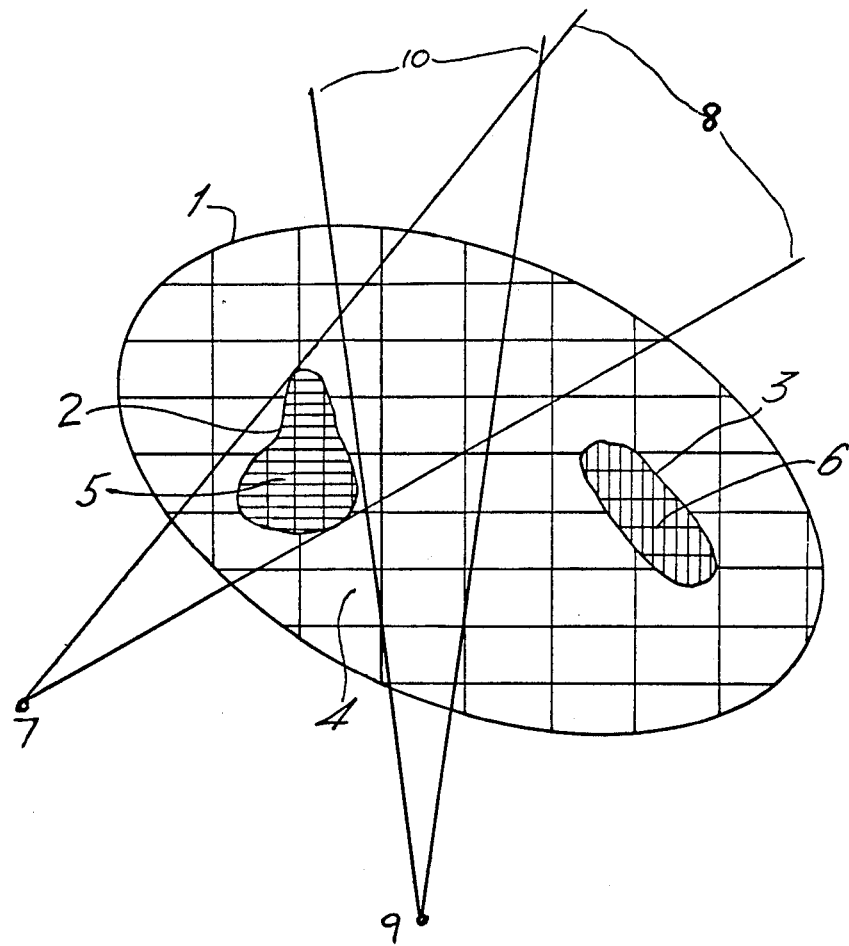
FIG. 1 is a schematic representation of a display of information obtained by echography.

An example of the use of the present invention is illustrated in FIG. 1 which is a schematic representation of a display of information obtained by echography. In the Figure, the outline 1 denotes the position of the outside border of the examined cross-section. Outlines 2 and 3 denote the positions of two internal structures. In a normal echogram all outlines would be white on a black background or black on a white background as previously described and the contrast of these outlines is dependent on the reflection coefficient of the interfaces of the internal structures. The areas 4, 5 and 6 would normally be the same colour as the background or a shade of grey depending on the echo texture obtained from the areas. Points 7 and 9 represent two typical transducer locations which scan sector shaped areas 8 and 10 respectively.

The present invention is embodied in the simultaneous display of other information on this basic display by the use of other display techniques. For example, the roughness, a scattering property of the reflector, may be displayed as a change in colour or hue of the outlines 1, 2 and 3. The ultrasonic velocity of propagation in regions 4, 5 and 6 may be displayed as the spacing between horizontal hatching lines within these areas. The attenuation of the ultrasonic pulse within the structures may be displayed as the spacing between vertical hatching lines. In the case where region 3 is the inside of a tube carrying moving liquid, for example a blood vessel, the velocity of motion of the liquid may be displayed by a relief presentation formed by replacing each dot by a short line in a particular direction, with the range of the line giving the velocity. The above-described means of display of each parameter are given by way of example only and each could be interchanged as required to optimise the system for various applications.

Figure 2:
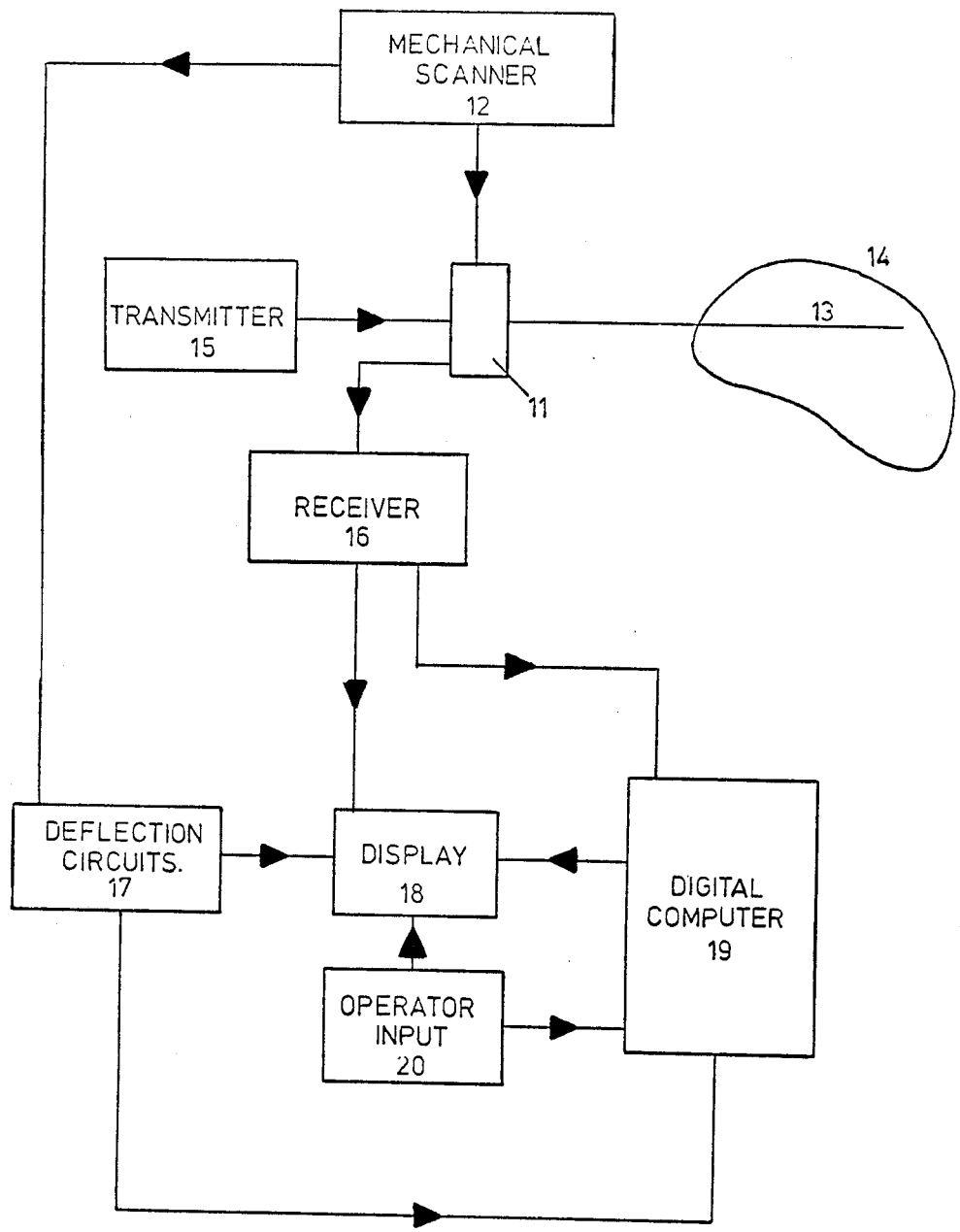
FIG. 2 illustrates a means for achieving the display of FIG. 1.

The means for achieving this display are illustrated in FIG. 2 in which the transducer 11 is made to perform its required scan by mechanical scanner 12 and its line of sight or beam axis 13 interrogates examined tissue 14. Transmitter 15 is used to pulse the transducer 11 and echoes are received by receiver 16 and processed for display. Deflection circuits 17 receive position information from mechanical scanner 12 and generate appropriate deflections on display 18. Up to this point the system is a standard ultrasonic pulse echo visualization system and its construction and operation are known to those skilled in the art and lead to the standard display of a black on white or white on black representation of the position of echo producing structures within the scanned anatomy 14 on the display 18. Signals from the receiver 16 and the deflection circuits 17 are also fed to the digital computer 19 where they may be processed to produce the required additional parameters for display. Using the operator input 20 which may be any of the standard means of computer graphics input such as a light pen, XY digitizer, joystick or other means, the operator defines on the display 18 the regions in which calculation of the parameters is required. This step is necessary as the techniques mentioned require the assumption that the parameter to be measured is constant within the nominated region. The computer then performs the signal analysis to be fed to the display system.

The following methods of extracting information regarding the various parameters are given as examples, as a variety of methods are possible. To extract velocity of propagation information, referring to FIG. 1 echo data are required for transducer positions 7 and 9, giving data in sector shaped regions 8 and 10. The sector 8 contains echoes which have transversed area of interest 5 which has been input to the computer through operator input 20 in FIG. 2. The analysis assumes that the velocity of propagation inside region 5 is a constant value $v1$ and that the velocity outside region 5 is constant and equal to a certain standard value $vo$ which depends on the part of the anatomy scanned.

The different velocity of propagation inside region 5 caused echoes displayed in sector 8 to be shifted towards or away from transducer 7. This shift can be determined by performing the well-known mathematical procedure of two-dimensional corss-correlation between the two sets of data in the region of overlap between areas 8 and 10. The component of $\partial$shift along the direction towards transducer position 7 called $\gamma t$ and the average thickness d of region 5 along the same direction are then used to compute the velocity $v1$ with the region 5 by the relationship $$v1 = \frac{vo}{1 - \frac{\delta t \cdot vo}{d}}$$

The method of extracting attenuation information also involves specification of a region and also specification of a direction of interest which may be defined by a transducer position. For example the operator would use operator input 20 to define region 5 and transducer position 7. A particular examination line of sight is taken and the amplitude of echoes as a function of time is examined. The echo amplitudes are converted to logarithmic scale as a function of time and a line of best fit through the logarithmic amplitudes is calculated by the well known method of least-squares. The slope of the line as a function of time is a measure of the attenuation and again is regarded as constant throughout the region.

Scattering information can be examined in terms of variation of echoes in a particular picture element from different directions. The transducer 7 is rotated so that the line of sight always traverses the same point but from different directions. The variation of echo size with angle has been shown to provide a characteristic which differs for different biological materials. This variation can be allocated a numerical value by the well-known digital signal processing techniques of taking the frequency spectrum of the characteristic and then taking the first or the second moment or a combination thereof of the frequency spectrum. This process provides a number representing scattering properties of each sampled point on the echogram.

The entire display is generated within the memory of digital computer 19. Information is output through five channels which are used in the display 18 to control X or horizontal deflection, Y or vertical deflection and brightness in up to three basic colours for a colour display or simple brightness in a black and white display. For example, the basic grey-scale echogram display which is the standard display in the present state of the art could be output with a rectangular X-Y deflection raster and intensity through all three colour channels, giving a black and white grey scale display. Colouring of the specified regions may be used to indicate either velocity or attenuation which is measured as described above. The colour display is made by outputting a signal to the appropriate combination of channels while the display deflection raster is within the specified regions. This is a straightforward operation using simple computer techniques. A specified region can be crosshatched either by generating the hatch lines as data on the original picture in the computer memory and displaying them as part of the picture or by displaying the picture data first and then providing another deflection raster to write the hatch lines separately.

Data such as scattering characteristics which is obtained only at selected points on the display may be displayed by a small spiral, which is an alternative form of cross-hatching. This spiral can have either size or colour as a parameter related to the scattering characteristic.

From the foregoing description it will therefore be appreciated that the present invention enables a more useful presentation of data acquired by ultrasonic examination of objects. While the invention has been described with reference to particular embodiments, it will be generally understood by those skilled in the art that various changes may be made without departing from the true spirit and scope of the invention. Examples of such changes include the use of the various parameter display methods of this invention in the one dimensional "A mode" type of display or in the "M mode" in which a one dimensional "A mode" trade is swept in time across the display to reveal the pattern of movement of a moving reflector.

We claim:

1. A method of displaying information obtained by ultrasonic echoscopic examination of an object, said examination comprising the steps of transmitting pulses of ultrasonic energy into the object and receiving echoes of said pulses of ultrasonic energy reflected by acoustic impedance discontinuities within the object, which method comprises forming a first display of information representative of the position of acoustic impedance discontinuities within said object, analyzing said echoes to obtain information representative of additional parameters such as velocity of propagation, scattering properties and attenuation characteristics of said object and simultaneously displaying in said first display said information representative of additional parameters of said object, wherein the additional information displayed in said first display is displayed by means of changes in gray scale.

2. A method of displaying information obtained by ultrasonic echoscopic examination of an object, said examination comprising the steps of transmitting pulses of ultrasonic energy into the object and receiving echoes of said pulses of ultrasonic energy reflected by acoustic impedance discontinuities within the object, which method comprises forming a first display of information representative of the position of acoustic impedance discontinuities within said object, analyzing said echoes to obtain information representative of additional parameters such as velocity of propagation, scattering properties and attenuation characteristics of said object and simultaneously displaying in said first display said information representative of additional parameters of said object wherein the additional information displayed in said first display is displayed by means of cross-hatching.

* * * * *